United States Patent [19]

Takashima et al.

[11] Patent Number: 4,853,249
[45] Date of Patent: Aug. 1, 1989

[54] METHOD OF PREPARING SUSTAINED-RELEASE PHARMACEUTICAL/PREPARATION

[75] Inventors: Yasuji Takashima, Ageo; Ikuo Koyama, Hasuda; Tooru Maki, Ageo; Katsu Nakamori, Tokyo, all of Japan

[73] Assignee: Taisho Pharmaceutical Co., Ltd., Japan

[21] Appl. No.: 928,370

[22] Filed: Nov. 10, 1986

[30] Foreign Application Priority Data

Nov. 15, 1985 [JP] Japan .................. 60-257302

[51] Int. Cl.⁴ .................................................. A61K 9/22
[52] U.S. Cl. ........................................ 427/3; 424/468
[58] Field of Search ................ 427/3; 424/19, 38, 468

[56] References Cited

U.S. PATENT DOCUMENTS

2,921,883 1/1960 Reese .
3,115,441 12/1963 Hermelin .
4,568,560 2/1986 Schobel .
4,572,833 2/1986 Pedersen .................................. 427/3
4,684,516 8/1987 Bhutani .................................. 427/3

Primary Examiner—Sam Silverberg
Attorney, Agent, or Firm—Lorusso & Loud

[57] ABSTRACT

A method of preparing a sustained-release pharmaceutical preparation, which comprises applying a solution of a binder in water or an alcohol and a fine powder of a hydrophobic solid material which does not easily dissolve within the stomach and intestines to the surface of solid particles containing a drug while the solid particles are being tumbled, thereby to coat the solid particles with the binder and the hydrophobic solid material.

16 Claims, 4 Drawing Sheets

METHOD OF PREPARING SUSTAINED-RELEASE PHARMACEUTICAL/PREPARATION

This invention relates to a method of preparing a sustained-release pharmaceutical preparation, and more specifically, to a simple and efficient method of preparing a sustained-release pharmaceutical preparation by coating solid particles containing a drug with a hydrophobic solid material.

Sustained-release pharmaceutical preparations in which the release of a drug is retarded have previously been known. They are generally obtained by coating the surface of drug-containing solid particles with a hydrophobic material, specifically, for example, by a method which comprises dissolving the hydrophobic solid substance in an organic solvent, spraying the resulting solution onto the surface of the drug-containing solid particles and then drying the particles, or a method which comprises spraying a heat-melted mass of the hydrophobic solid material directly onto the surface of the drug-containing solid particles without using an organic solvent.

Since the first-mentioned method requires the use of organic solvents toxic to humans, for example halogenated hydrocarbons such as carbon tetrachloride and chloroform, hydrocarbons such as hexane and benzene, lower alcohols such as methanol and propanol, and ketones such as acetone, many facilities are needed in order to secure safety on the working personnel and prevent atmospheric pollution during the production of sustained-release pharmaceuticals. Furthermore, since such organic solvents are used in relatively large amounts, a long time, for example, 8 to 10 hours, is required in order to remove these solvents from the coated pharmaceutical preparations. Hence, the efficiency of pharmaceutical preparation is very low.

On the other hand, the latter method developed in order to avoid these problems requires a melting pot for heat-melting the hydrophobic solid material and facilities for maintaining piping or a spray nozzle at a high temperature to avoid solidification of the molten hydrophobic material in the piping or spray nozzle. Furthermore, in order to coat the drug-containing solid particles uniformly with the hydrophobic material, the molten hydrophobic material should be sprayed in a very fine form. For this purpose, a high-pressure device for spraying liquid droplets under high pressure from the nozzle is required. Furthermore, according to this method, the cleaning operation after the coating operation is considerably time-consuming and reduces the overall working efficiency.

It is an object of this invention to provide a method of preparing a sustained-release pharmaceutical preparation which has overcome the aforesaid problems of the prior art.

A primary object of this invention is to provide a simple and easy method of preparing a sustained-release pharmaceutical preparation whose drug releasing is well sustained without using toxic organic solvents for dissolving the hydrophobic solid material and without the need for a melting pot for melting the hydrophobic substance, facilities for keeping piping or nozzles warm, high pressure nozzles, etc.

According to this invention, there is provided a method of preparing a sustained-release pharmaceutical preparation, which comprises applying a solution of a binder in water or an alcohol and a fine powder of a hydrophobic solid material which does not easily dissolve within the stomach and intestines to the surface of solid particles containing a drug while the solid particles are being tumbled, thereby to coat the solid particles with the binder and the hydrophobic solid material.

The drug-containing solid particles to which the sustained-release coating is applied in accordance with the method of this invention are produced by molding at least one drug (pharmacologically active substance) together with adjuvants customarily used in the production of solid pharmaceutical preparations, for example excipients such as corn starch, potato starch, lactose and mannitol, lubricants such as meta-silicate, magnesium aluminate, light anhydrous silicic acid and talc, disintegrants such as carboxymethyl cellulose calcium, low substituted hydroxypropyl cellulose and microcrystalline cellulose, and binders such as hydroxypropyl cellulose, hydroxyropyl methyl cellulose and polyvinylpyrrolidone. The solid particles may be in any desired form such as granules, mini-pellets and pills. The suitable size of the solid particles, in terms of average particle diameters, is generally within the range of 250 to 3000 microns, preferably 500 to 1500 microns. These solid particles may also be crystals or other solid particles of the drug itself if they are in a similar form. There is no restriction on the drug which can be included in such solid particles if it is desired to be released slowly within the body of mammals. Specific examples are analgesic anti-inflammatory agents such as indomethacin, ibprofen and acetaminophen, antihistaminics such as chlorophenylamine maleate, agents for the circulatory system such as nifedipine, isosorbitol nitrate and propranolol, antibiotics such as cephalexin, iron preparations such as ferrous fumarate, anti-asthema agents such as theophylline, potassium preparations such as potassium chloride, tranquilizers such as thioridazine hydrochloride, muscle relaxants such as chlorphenesin carbonate and anti-mania agents such as lithium carbonate.

The drug-containing solid particles may be prepared by using a known tumbling agglomeration method, for example by charging sugar crystals having a size of 40 to 50 mesh into a tumbling granulator, and spraying the binder solution onto the sugar crystals and simultaneously sprinkling the drug and the adjuvants.

The method of this invention is conveniently carried out in a suitable tumbling device by using the drug-containing solid particles prepared as above.

In the method of this invention, the aqueous or alcohol solution of the binder and the fine powder of a hydrophobic solid material which does not easily dissolve within the stomach and intestines are applied to the drug-containing solid particles prepared as above while the drug-containing solid particles are being tumbled in a tumbling granulator. In one preferred embodiment of the method, the binder solution is sprayed onto the solid particles being tumbled, and nearly simultaneously with the spraying, the fine powder of the hydrophobic solid material is sprinkled little by little; or immediately after a predetermined amount of the binder solution has been sprayed, the fine powder of the hydrophobic solid substance is sprinkled, and as required, this operation is repeated. The fine powder of the hydrophobic solid substance adheres to the surface of the solid particles wetted with the binder solution to cover the surface of the solid particles.

The solid particles covered with the hydrophobic solid substance are dried to remove the solvent used in the binder solution. The drying temperature is generally about 40° to 70° C., preferably about 60° to 70° C., depending upon the type of the solvent, and the drying time is usually about 0.5 to 1 hour.

The binder used in the method of this invention includes pharmaceutically acceptable polymeric substances soluble in water or alcohol. Illustrative are cellulose derivatives such as methyl cellulose, ethyl cellulose, hydroxymethyl cellulose, hydroxyethyl cellulose, hydroxypropyl cellulose and hydroxypropylmethyl cellulose, and water-soluble synthetic polymeric substances such as polyvinylpyrrolidone and polyvinyl alcohol. They may be used singly or in combination. Methyl cellulose and ethyl cellulose are especially suitable.

The solvent for dissolving the binder may be water or a nontoxic alcohol such as ethanol.

The content of the binder in the solvent is not strictly restricted, and may be varied depending upon the type or form of the drug-containing solid particles, the type of the binder and the type of the hydrophobic solid material.

The application of the binder solution to the drug-containing solid particles can be effected by, for example, spraying from a spray nozzle.

The hydrophobic solid materials used in the method of this invention are not easily dissolved within the stomach and intestines include normally solid materials which can permit slow release of the drug from the drug-containing solid particles through the coating formed of it and the binder. Pharmaceutical lipophilic organic solid materials having a melting point of 50° to 90° C. are especially suitable. Such a hydrophobic solid material can be selected from, for example, higher alcohols, higher fatty acids, higher fatty acid glycerin esters, oils and fats, waxes, and higher hydrocarbons which are solid at room temperature.

Examples of the higher alcohols include cetyl alcohol, 14-methylhexadecanol-1, stearyl alcohol, 16-methyloctadecanol-1, eicosanol-1, 18-methylnonadecanol-1, 18-methyleicosanol-1, docosanol-1, 20-methylheneicosanol-1, 20-methyldocosanol-1, tetracosanol-1, 22-methyltricosanol-1, 22-methyltetracosanol-1, 24-methylpentancosanol-1, 4-methylhexacosanol-1, octacosanol-1, nonacosanol-1, myricyl alcohol, and cholesterol. Preferred higher alcohols have 16 to 26 carbon atoms, and stearyl alcohol is especially preferred.

Examples of the higher fatty acids are myristic acid, palmitic acid, stearic acid, behenic acid and 12-hydroxystearic acid. Preferred higher fatty acids have 14 to 22 carbon atoms, and stearic acid are especially preferred.

Examples of the glycerin esters of higher fatty acids are monoglycerides, diglycerides and triglycerides of higher fatty acids.

Examples of the oils and fats are hardened soybean oil, hardened castor oil, Japan wax, hardened beef tallow, hardened lard. Hardened castor oil is especially preferred.

Examples of the waxes are carnauba wax, hard lanolin, candelila wax, and beeswax. Of these, carnauba wax is especially preferred.

Examples of the higher hydrocarbons are hydrocarbons having 16 to 70 carbon atoms such as paraffin, ceresin, and microcrystalline wax. Paraffin is especially preferred.

The hydrophobic solid material is used in fine powder form. Its particle diameter should be sufficiently smaller than the particle diameter of the drug-containing solid particles. Desirably, the average particle diameter of the hydrophobic solid material is generally not more than 100 microns, preferably 10 to 30 microns. By properly selecting the particle diameter of the hydrophobic solid material and the amount of it adhering to the drug-containing solid particles, the release of the drug from the drug-containing solid particles can be controlled.

The amounts of the binder and the fine hydrophobic solid material are not stricted limited, and may be varied depending upon the type of the drug, the form or size of the drug-containing solid particles, the type of the binder, and the type or particle diameter of the hydrophobic solid material. Generally, the binder is conveniently used in an amount of 1 to 30 parts by weight, preferably 5 to 15 parts by weight, per 100 parts by weight of the hydrophobic solid material. The hydrophobic solid material is used desirably in an amount of 5 to 60 parts by weight, preferably 10 to 40 pars by weight, per 100 parts by weight of the drug-containing solid particles so that the surface of the drug-containing solid particles is uniformly coated with the fine powder of the hydrophobic solid material.

By drying the drug-containing solid particles coated with the binder and the fine powder of the hydrophobic solid material under the conditions described hereinabove, the desired sustained-release pharmaceutical preparation can be obtained.

According to this invention, the sustained-release coating composed of the binder and the hydrophobic solid material can be made denser by heat-treating the so prepared pharmaceutical preparation at a temperature above the melting point of the hydrophobic solid material and desirably up to 30° C. plus the melting point. This heat-treatment can be carried out at temperatures within the aforesaid range, preferably 70° to 90° C., for a period of about 0.5 to 10 hours, preferably 1 to 3 hours.

By properly choosing the amount and particle diameter of the hydrophobic solid material and the heat-treating conditions, it is possible to adjust the thickness and the degree of denseness of the sustained-release coating on the drug-containing solid particles and thereby to control the release of the drug from the solid particles to the desired degree.

The heat-treatment may, for example, be carried out by using a fluidized bed dryer.

According to the method of this invention described above, a pharmaceutical preparation having excellent sustained drug release characteristics can be obtained economically, conveniently and easily without using any special device.

The following Examples and Test Examples illustrate the present invention more specifically.

EXAMPLE 1

By the tumbling granulation method, 290 g of a 5% aqueous solution of hydroxypropyl cellulose as a binder was gradually sprayed onto 200 g of sugar crystals having a size of 40 to 50 mesh. Simultaneously, a mixed powder of 300 g of anhydrous caffeine and 500 g of corn starch was gradually sprinkled. After applying, the granules were dried at 60° C. for 1 hour, and by using a sieve, spherical granules having a particle diameter of 16 to 32 mesh and containing caffeine were prepared.

A tumbling granulator having a diameter of 36 cm was rotated at a rate of 150 rpm, and 500 g of the caffeine-containing spherical granules obtained above were fed into the granulator. While the granules were tumbled, a solution of 8 g of ethyl cellulose as a binder in 198 g of ethanol was sprayed at a rate of 20 ml/min. and at the same time 100 g of hardened castor oil having an average particle diameter of 30 microns was gradually sprinkled to complete the coating.

The coated granules were dried at 70° C. for 1 hour to obtain a sustained-release pharmaceutical preparation (pharmaceutical peparation 1).

EXAMPLE 2

A sustained-release pharmaceutical preparation (2) was obtained in the same way from 15 g of ethyl cellulose, 360 g of ethanol, 500 g of the same spherical granules (caffeine content 300 mg/g) as used in Example 1 and 200 g of hardened castor oil having an average particle diameter of 30 microns.

EXAMPLE 3

A sustained-release pharmaceutical preparation (3) was obtained in the same way as in Example 1 from 22 g of ethyl cellulose, 528 g of ethanol, 500 g of the same spherical granules (caffeine content 300 mg/g) as used in Example 1 and 300 g of hardened castor oil having an average particle diamettter of 30 microns.

EXAMPLE 4

A sustained-release pharmaceutical preparation (4) was obtained in the same way as in Example 1 except that 100 g of carnauba wax having an average particle diameter of 15 microns was used instead of 100 g of the hardened castor oil.

EXAMPLE 5

A sustained-release pharmaceutical preparation (5) was prepared in the same way as in Example 2 except that 200 g of carnauba wax having an average particle diameter of 15 microns was used instead of 200 g of the hardened castor oil.

EXAMPLE 6

A sustained-release pharmaceutical preparation (6) was prepared in the same way as in Example 3 except that 300 g of carnauba wax having an average particle diameter of 15 microns was used instead of 300 g of the hardened castor oil.

EXAMPLE 7

A sustained-release pharmaceutical preparation (7) was prepared in the same way as in Example 1 except that 100 g of stearic acid having an average particle diameter of 20 microns was used instead of 100 g of the hardened castor oil.

EXAMPLE 8

A sustained-release pharmaceutical preparation (8) was prepared in the same way as in Example 2 except that 200 g of stearic acid having an average particle diameter of 20 microns was used instead of 200 g of the hardened castor oil.

EXAMPLE 9

A sustained-release pharmaceutical preparation (9) was prepared in the same way as in Example 3 except that 300 g of stearic acid having an average particle diameter of 20 microns was used instead of 300 g of the hardened castor oil.

EXAMPLE 10

A sustained-release pharmaceutical preparation (10) was prepared in the same way as in Example 1 except that 100 g of stearyl alcohol having an average particle diameter of 25 microns was used instead of 100 g of the hardened castor oil.

EXAMPLE 11

A sustained-release pharmaceutical preparation (11) was prepared in the same way as in Example 2 except that 200 g of stearyl alcohol having an average particle diameter of 25 microns was used instead of 200 g of the hardened castor oil.

EXAMPLE 12

A sustained-release pharmaceutical preparation (12) was prepared in the same way as in Example 3 except that 300 g of stearyl alcohol having an average particle diameter of 25 microns was used instead of 300 g of the hardened castor oil.

EXAMPLE 13

A sustained-release pharmaceutical preparation (13) was prepared in the same way as in Example 1 except that 100 g of paraffin having an average particle diameter of 30 microns was used instead of 100 g of the hardened castor oil.

EXAMPLE 14

A sustained-release pharmaceutical preparation (14) was prepared in the same way as in Example 2 except that 200 g of paraffin having an average particle diameter of 30 microns was used instead of 200 g of the hardened castor oil.

EXAMPLE 15

A sustained-release pharmaceutical preparation (15) was prepared in the same way as in Example 3 except that 300 g of paraffin having an average particle diameter of 30 microns was used instead of 300 g of the hardened castor oil.

Figure 1:
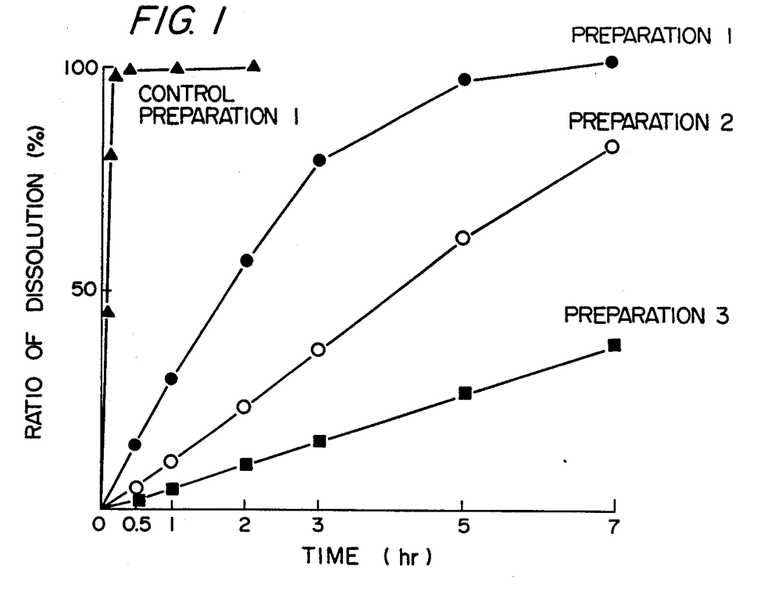

The dissolution of caffeine was examined using the spherical granules (caffeine content 300 mg/g) used in Example 1 as a control preparation 1, and pharmaceutical preparations 1 to 3 obtained in Example 1 to 3 in accordance with JPX dissolution test method, second method (purified water was used as a test liquid, and the amount of caffeine dissolved from the sample into the test liquid at an appropriate time was measured). The results are shown in FIG. 1.

TEST EXAMPLE 2

Figure 2:
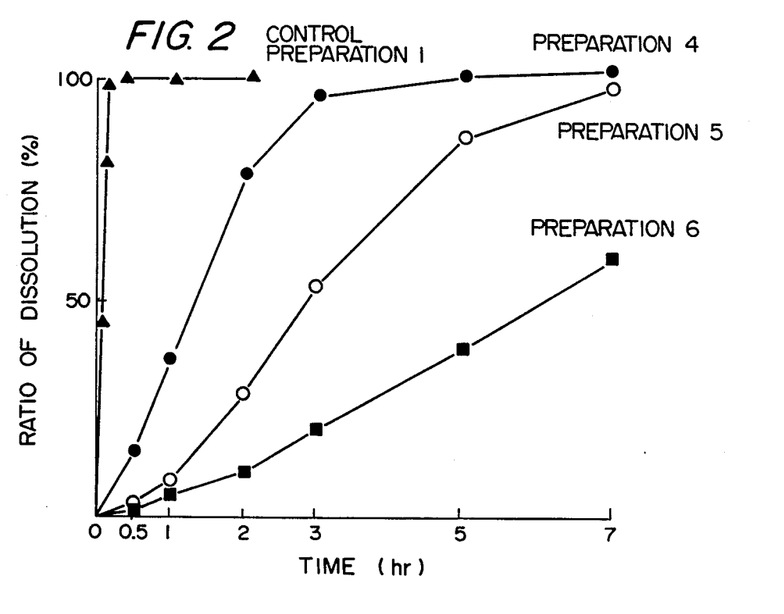

Pharmaceutical preparations 4 to 6 obtained in Examples 4 to 6 and control preparation 1 were subjected to the same test as in Test Example 1 to examine the dissolution of caffeine. The results are shown in FIG. 2.

TEST EXAMPLE 3

Figure 3:
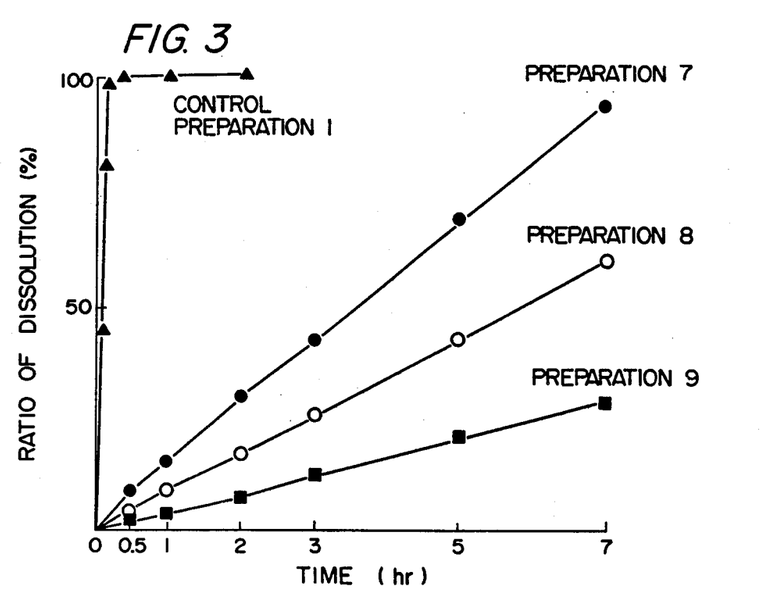

Pharmaceutical preparations 7 to 9 obtained in Examples 7 to 9 and control preparation 1 were subjected to the same test as in Test Example 1 to examine the dissolution of caffeine. The results are shown in FIG. 3.

TEST EXAMPLE 4

Figure 4:
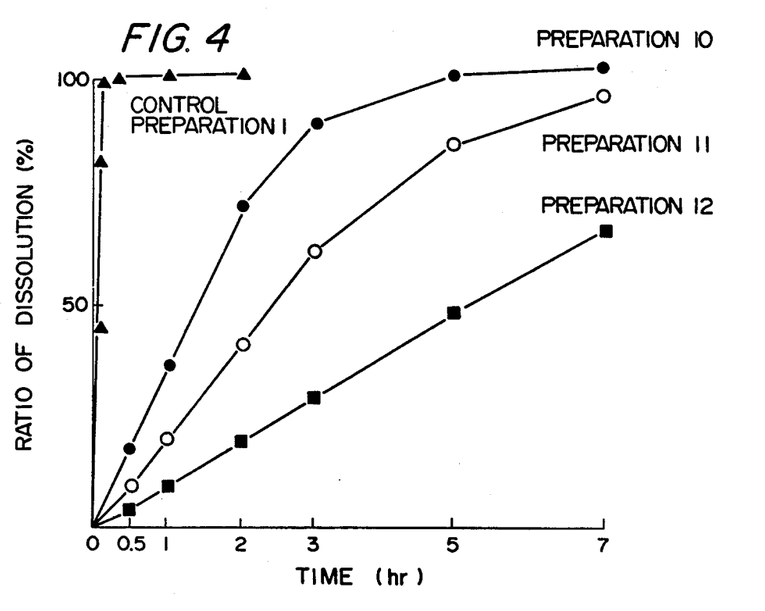

Pharmaceutical preparations 10 to 12 obtained in Examples 10 to 12 and control preparation 1 were subjected to the same test as in Test Example 1 to examine the dissolution of caffeine. The results are shown in FIG. 4.

TEST EXAMPLE 5

Figure 5:
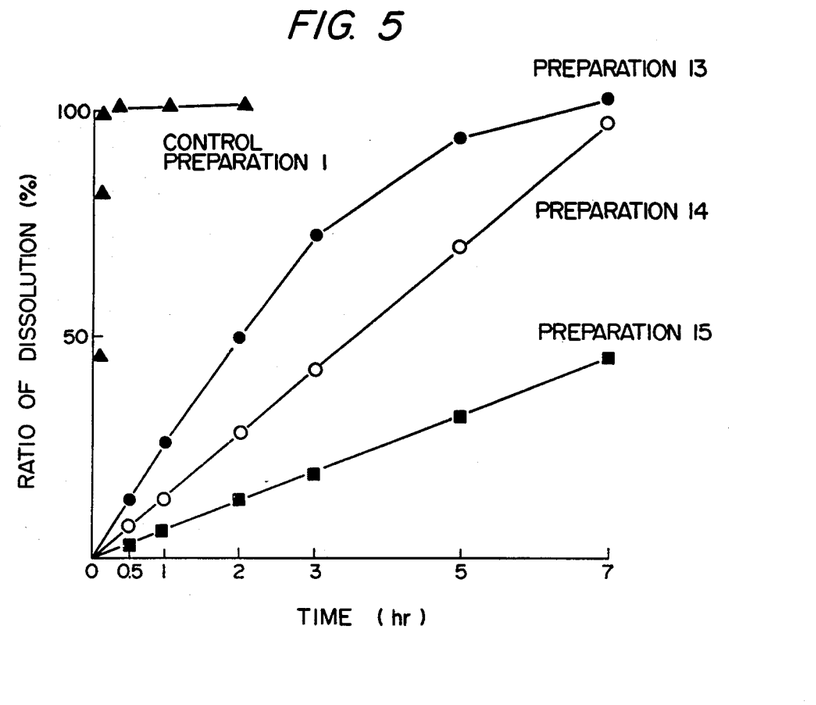

Pharmaceutical preparations 13 to 15 obtained in Examples 13 to 15 and control preparation 1 were subjected to the same test as in Test Example 1 to examine the dissolution of caffeine. The results are shown in FIG. 5.

EXAMPLE 16

(1) Ethyl cellulose (8 g) was dissolved in 192 g of ethanol to prepare 200 g of a binder solution.

In a coating device, 500 g of the same spherical granules having a size of 16 to 32 mesh (caffeine content 300 mg/g) as used in Example 1 were tumbled, and the binder solution was sprayed onto these granules. Simultaneously, 100 g of hardened castor oil having an average particle diameter of 30 microns was gradually sprinkled onto the surface of the spherical granules. The coated granules were dried at 60° C. for 1 hour to obtain granules (A).

(2) The granules (A) obtained in (1) were heat-treated at 80° C. for 1 hour to obtain a sustained pharmaceutical preparation (16).

EXAMPLE 17

A sustained-release pharmaceutical preparation (17) was obtained by heat-treating the granules (A) obtained in Example 16, (1) at 80° C. for 3 hours as in accordance with Example 16, (2).

EXAMPLE 18

A sustained-release pharmaceutical preparation (18) was obtained by heat-treating the granules (A) obtained in Example 16, (1) at 90° C. for 1 hour as in accordance with Example 16, (2).

EXAMPLE 19

A sustained-release pharmaceutical preparation (19) was obtained by heat-treating the granules (A) obtained in Example 16, (1) at 90° C. for 3 hours as in accordance with Example 16, (2).

EXAMPLE 20

(1) Granules (B) were prepared as in Example 16, (1) except that 100 g of carnauba wax having an average particle diameter of 15 microns were used instead of 100 g of the hardened castor oil.

(2) A sustained-release pharmaceutical preparation (20) was obtained by heat-treating the granules (B) obtained in (1) above in accordance with Example 16, (2).

EXAMPLE 21

A sustained-release pharmaceutical preparation (21) was obtained by heat-treating the granules (B) obtained in Example 20, (1) at 80° C. for 3 hours in accordance with Example 20, (2).

EXAMPLE 22

A sustained-release pharmaceutical preparation (22) was obtained by heat-treating the granules (B) obtained in Example 20, (1) at 90° C. for 1 hour in accordance with Example 20, (2).

EXAMPLE 23

A sustained-release pharmaceutical preparation (23) was obtained by heat-treating the granules (B) obtained in Example 20, (1) at 90° C. for 3 hours in accordance with Example 20, (2).

TEST EXAMPLE 6

Figure 6:
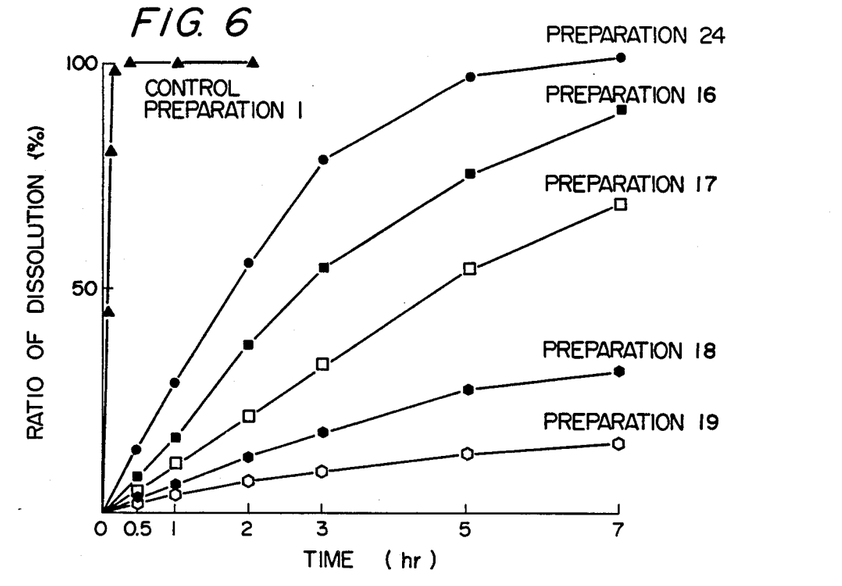

The dissolution of caffeine was examined in the same way as in Test Example 1 using the spherical granules (caffeine content 300 mg/g) used in Example 1 as a control preparation 1, the granules (A) obtained in Example 20, (1) as pharmaceutical preparation 24, and also the pharmaceutical preparations 16 to 19 obtained in Examples 16 to 19. The results are shown in FIG. 6.

TEST EXAMPLE 7

Figure 7:
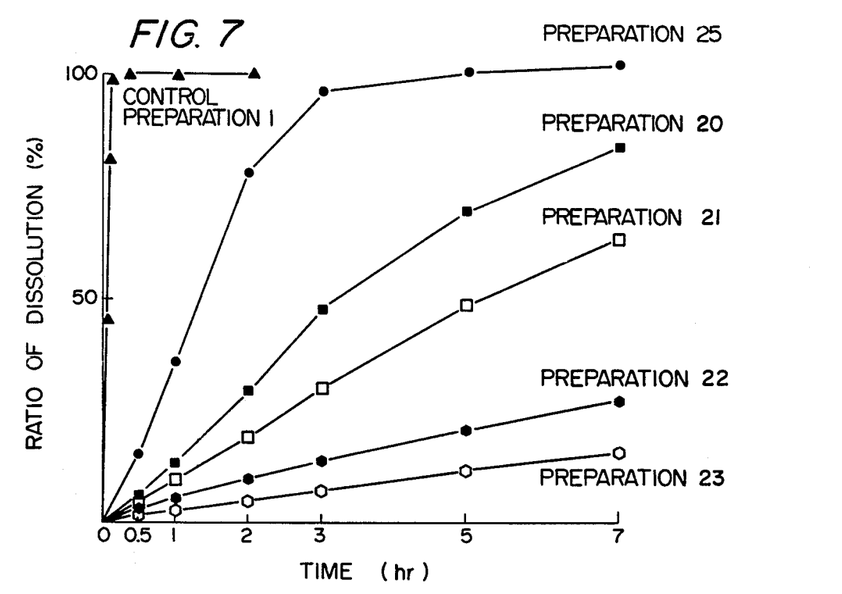

The dissolution of caffeine was examined in the same way as in Test Example 1 using the granules (B) prepared in Example 20, (1) as pharmaceutical preparation 25, and also the pharmaceutical preparations 20 to 23 obtained in Examples 20 to 23. The results are shown in FIG. 7.

What is claimed is:

1. A method of preparing a sustained-release pharmaceutical preparation, said method comprising:
   providing solid particles containing a drug;
   tumbling said drug-containing solid particles;
   applying to the surfaces of the tumbling drug-containing particles a solution of 1–30 parts by weight of a binder in water or an alcohol to wet the surfaces of the tumbling drug-containing particles;
   simultaneously with application of said binder, separately applying 100 parts by weight of a fine powder of a hydrophobic solid material, which does not easily dissolve within the stomach and intestines, to the wetted surfaces of said drug-containing particles to thereby coat said solid particles with said binder and said hydrophobic solid material; and
   heating the coated particles to a temperature ranging from the melting point of said hydrophobic solid material to 30° C. above said melting point.

2. The method of claim 1 wherein the binder is a pharmaceutically acceptable polymeric substance which is soluble in water or in the alcohol.

3. The method of claim 2 wherein the polymeric substance is methyl cellulose or ethyl cellulose.

4. The method of claim 1 wherein the alcohol is ethanol.

5. The method of claim 1 wherein the hydrophobic solid material is selected from higher alcohols, higher fatty acids, higher fatty acid glycerides, oils and fats, waxes and higher hydrocarbons which are solid at room temperature.

6. The method of claim 5 wherein the hydrophobic solid material is selected from stearyl alcohol, stearic acid, hardened castor oil, carnauba wax and paraffin.

7. The method of claim 1 wherein the solid particles are in the form of granules, minipellets or pills.

8. A method in accordance with claim 1 wherein said tumbling is by use of a tumbling granulator.

9. A method in accordance with claim 1 wherein said binder solution is first applied to wet the surfaces of said drug-containing particles and then the hydrophobic solid material is applied.

10. A method in accordance with claim 1 wherein said binder solution is sprayed to wet the surfaces of said drug-containing solid particles and said fine powder is then sprinkled onto said wetted drug-containing particles.

11. A method in accordance with claim 1 wherein said drug-containing solid particles have an average particle diameter of 250 to 3000 microns and said fine powder has an average particle diameter of not more than 100 microns.

12. A method in accordance with claim 1 wherein said drug-containing solid particles have an average particle diameter of 500–1500 microns and said fine powder has an average particle diameter of 10–30 microns.

13. A method in accordance with claim 1 wherein 5–60 parts by weight of the fine powder of hydrophobic material is applied per 100 parts by weight of said drug-containing particles.

14. A method in accordance with claim 1 wherein 5–15 parts by weight of said binder is applied per 100 parts by weight of said hydrophobic material and 10–40 parts by weight of said hydrophobic material is applied per 100 parts by weight of said drug-containing particles.

15. The method of claim 1 wherein said temperature is 70°–90° C.

16. The method of claim 1 wherein said heating is continued for a time period of 0.5 to 19 hours and wherein said time period, said temperature and the particle size of the hydrophobic material are selected to given a coating of the hydrophobic solid of a predetermined thickness.

* * * * *

UNITED STATES PATENT AND TRADEMARK OFFICE
CERTIFICATE OF CORRECTION

PATENT NO.  : 4,853,249
DATED       : August 1, 1989
INVENTOR(S) : Takashima et al It is certified that error appears in the above—identified patent and that said Letters Patent is hereby corrected as shown below:

Col. 2, line 37 "carbonate" should read -- carbamate--.

Col. 5, line 52 delete "25".

Col. 10, line 12(claim 16, line 2) "19" should read --10--

Signed and Sealed this

Twenty-eighth Day of January, 1992

Attest:

HARRY F. MANBECK, JR.

*Attesting Officer*   *Commissioner of Patents and Trademarks*